(12) United States Patent
David

(10) Patent No.: US 7,613,343 B2
(45) Date of Patent: Nov. 3, 2009

(54) NOSOLOGIC SYSTEM OF DIAGNOSIS

(75) Inventor: Ronald B. David, Mechanicsville, VA (US)

(73) Assignee: Kilimanjaro Partnership, Berwyn, PA (US)

( * ) Notice: Subject to any disclaimer, the term of this patent is extended or adjusted under 35 U.S.C. 154(b) by 0 days.

(21) Appl. No.: 12/199,274

(22) Filed: Aug. 27, 2008

(65) Prior Publication Data
US 2009/0083068 A1 Mar. 26, 2009

Related U.S. Application Data

(63) Continuation of application No. 11/001,099, filed on Dec. 1, 2004, now Pat. No. 7,433,520.

(51) Int. Cl.
G06K 9/62 (2006.01)
G06K 9/00 (2006.01)

(52) U.S. Cl. .................................. 382/224; 382/133
(58) Field of Classification Search ............... 382/128, 382/133, 159, 224, 305; 600/9, 300; 707/7
See application file for complete search history.

(56) References Cited

U.S. PATENT DOCUMENTS

| | | | | |
|---|---|---|---|---|
| 5,887,588 | A * | 3/1999 | Usenius et al. ............... | 600/410 |
| 6,273,854 | B1 * | 8/2001 | Kane et al. ................... | 600/300 |
| 6,290,638 | B1 * | 9/2001 | Canedo et al. ................ | 600/9 |
| 6,482,156 | B2 * | 11/2002 | Iliff ............................ | 600/300 |
| 6,746,398 | B2 * | 6/2004 | Hervy et al. ................. | 600/300 |
| 6,750,011 | B1 * | 6/2004 | Perlin .......................... | 435/6 |
| 6,774,217 | B1 * | 8/2004 | Croce et al. ............ | 530/388.26 |
| 6,807,583 | B2 * | 10/2004 | Hrischuk et al. ............ | 719/318 |
| 7,149,756 | B1 * | 12/2006 | Schmitt et al. ............ | 707/104.1 |
| 2003/0092040 | A1 * | 5/2003 | Bader et al. ..................... | 435/6 |
| 2003/0154105 | A1 * | 8/2003 | Ferguson ....................... | 705/2 |
| 2003/0217037 | A1 * | 11/2003 | Bicker et al. ................... | 707/1 |
| 2004/0102525 | A1 * | 5/2004 | Kozachuk .................. | 514/662 |
| 2004/0193036 | A1 * | 9/2004 | Zhou et al. ................. | 600/407 |
| 2005/0096311 | A1 * | 5/2005 | Suffin et al. ................ | 514/217 |

FOREIGN PATENT DOCUMENTS

WO US99/26521 * 11/1999

(Continued)

OTHER PUBLICATIONS

David, Ronald B. (Ed.), "Child and Adolescent Neurology," Mosby's Neurology Psychiatry Access Series,1998, exemplary excerpts including pp. v, vi, xi, xiii, xiv, xv, 3-13, 29-52, 53-85,160-161,183-224, 295-358, 239-377, and 507-537.*

(Continued)

Primary Examiner—Daniel G Mariam
(74) Attorney, Agent, or Firm—Woodcock Washburn LLP

(57) ABSTRACT

Nosologic classification of diseases is accessible on line in a computer system. A computer data base has records of discriminating features, consistent features and variable features of known afflictions. The features are in classification domains which include a phenomenologically classified domain, classified by listing commonly agreed on observations and distinguishing between entities based on these observations. Other classification domains are anatomically classified, pathologically classified by the gross of microscopic pathologic anatomy, revealed by either traditional pathologic study or imaging. One of the classification domains is pathophysiologically, by demonstrating altered chemical or electrophysiological parameters. At least one of the classification domains is classified ethiologically by cause.

1 Claim, 2 Drawing Sheets

FOREIGN PATENT DOCUMENTS

WO        WO 02/28460     *     4/2002

OTHER PUBLICATIONS

David, Ronald B. (Ed.), "Pediatric Neurology for the Clinician," Appleton & Lange, Norwald, CT, 1992, exemplary excerpts to include pp. xi-xxii, 153-168, 174, and 181.*
Venter G. et al., "The Human Genome," Science 2000, vol. 291, Feb. 16, 2001, 1304-1351.*
"Initial Sequencing and Analysis of the Human Genome," The Genome International Sequencing Consortium, Nature, vol. 409, Feb. 15, 2001, 860-921.*
Mironov, A., et al. "Frequent Alternative Splicing of Human Genes," Genome Research, 9(12), Dec. 4, 1999, 1288-1293.*
McGee, M., "Fix Of A Sick System", Information Week, Dec. 15, 2003.*
Snyder, Bill, 'qq0 Slack in Government IT Demand, TheStreet.com, Feb. 5, 2003, 1-2.*
Rogoski, R., "LIS and the Enterprise," Health Management Technology, Feb. 2003, 1-6.*
General of the America Association 79, 1200-1205 (1998).*
Scurf, J., et al., "Frequency and Prevention of Symptomless Deepvein Thrombosis in Long Haul Flights: a Randomized Trial," The Lancet 357, 1485-1489, Mar. 2001.*
"Accessing the Celera Human Genome Sequence Data"; Science Magazine; Feb. 14, 2004; http://www.scincemag.org/feature/data/announcement/gsp.shl.*
Collins,Francis S., M.D., Ph.D., "The Human Genome Project: How Private Sector Developments Affect the Government Program"; Jun. 17, 1998; http ://www.house.gov/science/collins 06-17.htm.*
http://www.cdc.gov/nchs/datawh/ftpserv/ftpicd9/ftpicd9.htm#guidelines; Oct. 1, 2003.*

* cited by examiner

NOSOLOGIC SYSTEM OF DIAGNOSIS

FIELD OF THE INVENTION

This invention relates to a database of nosologic features in classification domains for use by physicians in the diagnosis of patients.

BACKGROUND OF THE INVENTION

Nosology is the branch of medical science that deals with the orderly classification of diseases.

While the practice of medicine has experienced major technological advances in recent years, nosologic systems (e.g. International Classification of Diseases-10 and the Diagnostic and Statistical Manual-IV of the American Psychiatric Association) present at times a confusing array of diagnostic possibilities. Many diseases/disorders may even be represented in more than one place in the diagnostic system. Lack of a comprehensive framework leads to diagnostic confusion in the clinical teaching and often in the research setting. Clearly organization and orderliness are needed to better discriminate between entities.

Classification issues have historic roots. Hippocrates suggested that "whoever undertakes to speak or write on medicine, should have first laid themselves some hypothesis as to their argument, such as hot or cold or moist or dry or whatever else they choose, thus reducing their subject within a narrow compass." The work of Thomas Sydenham on acute diseases first published in 1675 is seminal. Sydenham suggested that all diseases can be classified as to a certain definite species in the same manner as botanists describe their plants. He further suggested that pathologic phenomena should be described in precise detail in the same way a portrait painter seeks to capture the likeness of a subject. He also noted that particular and constant symptoms should be distinguished from accidental phenomena. John Locke, in describing Sydenham, suggested that he had a poor opinion of those who attempted to look at disease from a chemical point of view. On the other hand, he noted that Sydenham recognized the utility of chemotherapeutics, recognizing, for instance, that certain chemicals could induce vomiting, implying that treatment outcome was not a good basis for classification but overlooking its potential value as validator of diagnosis.

Carl Linné graduated as a Doctor of Medicine in 1735. While he is best known for his biological classification system (e.g. phyla, genera, species), his attempt to use this approach for medicine was never widely accepted, principally because of a confusion between the definitions of symptom and disease. Laennec in 1826 was among the first to link symptoms to pathologic anatomy when he described the disseminated pathology of tuberculosis. In the mid-Nineteenth Century, the pathophysiologic basis of disease came into focus. Methods for counting cells, methods for the measurement of the color of blood as well as methods for the examination of urine were developed. In the late $19^{th}$ century, an etiologic approach for the classification of disease became possible with the identification of a specific bacteria as the cause for a specific disease (Koch-Pasteur). This became the best first good example of using the best and most robust discriminator, etiology. There was, therefore, an evolutionary progression from phenomenologic descriptions to those which were base on etiology. Each reflected at the time the state of knowledge.

Many disorders in psychiatry and neurology still can only be described phenomenologically. While seemingly the least robust, pheomenologic validity is attainable. Skinner suggested that a phenomenologically based system should have certain features so as to make descriptions of specific entities valid. These include reliability; that is, agreement across examiners using the same diagnostic methodology; coverage, referring to the applicability of the classification domain of the patents for which it was intended; descriptive validity implying homogeneity in characterizing behavioral symptoms, personality characteristics, social history data, and other kinds of information which are used to make a diagnosis and lastly; predictive validity where a classification system can determine the potential effectiveness of treatment or the natural history of a psychiatric disorder. While Skinner's conceptual framework was meant to be applied to psychiatric disorders described phenomenologically, it can obviously be generalized. It can also provide a mechanism for a classification system.

Classification in science is important to medicine. A successful and, therefore, useful classification should be simple and easy to use. It should be organized hierarchically and have the flexibility to reflect the state of the art as it evolves. The disease/disorder should be defined etiologically through the rigorous application of the scientific method.

Texts and text book series have proposed an orderly classification of features used in diagnosis.

Accordingly, it is an object of the present invention to provide a computer based classification system which can be used by physicians in the diagnosis of patients.

SUMMARY OF THE INVENTION

In accordance with the present invention, a computer database has records of discriminating features, consistent features, and variable features of known afflictions. If a disease/disorder exists there must also exist features which discriminate it from similar entities. Features are clinically derived by expert opinion, categorical and multi-dimensional. Where the state-of-the-art permits, discriminators have been empirically validated.

In accordance with the invention the features are in testing classification domains.

Further in accordance with the invention the classification domains are defined according to the following schema.

1. Phenomenologically, by listing commonly agreed on observations and distinguishing between entities based on these observations. A good example is the clinical classification of epilepsies.
2. Anatomically, by site of origin of the disorder.
3. Pathologically, by the gross or microscopic pathologic anatomy, revealed by either traditional pathologic study or imaging.
4. Pathophysiologically, by demonstrating altered chemical or electrophysiological parameters.
5. Etiologically, by cause.

Under these general domains, sub domains can be identified; e.g., histopathology versus radio logic pathology. Much of the confusion that arises in diagnosis occurs when the clinician crosses classification domains. For example, the inclusion of an anatomically oriented "temporal lobe seizure" in a phenomenolgically based classification system that includes complex partial seizures. It is, therefore, extremely important from both a clinical and research standpoint that the classification domain to use should be pre-determined and contrasting discriminators be comparable (i.e. bacterial meningitides should not be enmeshed with viral meningitides). For a disease/disorder to exist, it must have some feature or features which discriminate between it and similar entities. Discriminating features may have inclusionary as well as exclusionary features. The ideal is to have a single discriminator. This then makes the contrast between a particular and similar entities more robust. When there is more than a single discriminator involved, this in essence becomes a criterion based system. While this is obviously less robust, a criterion based system may simply reflect the state-of-art.

The foregoing and other objects, features, and advantages of the invention will be better understood by the following more detailed description, drawings and claims.

DETAILED DESCRIPTION OF ILLUSTRATIVE EMBODIMENTS

Figure 1:
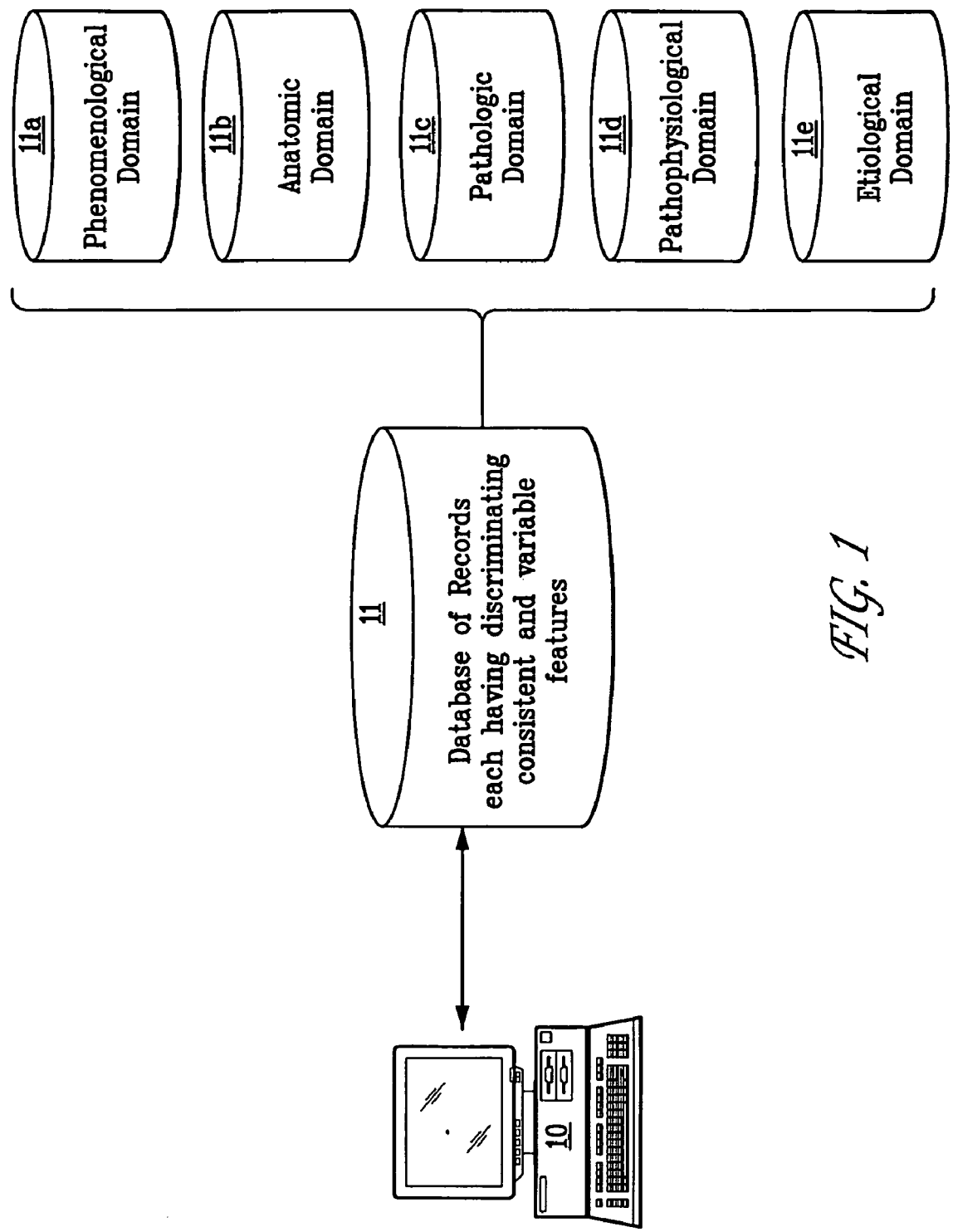
FIG. 1 depicts a computer and the database of the present invention.

FIG. 1 shows a computer system in which a personal computer 10 accesses the database 11 of the present invention. The database 11 has records of features which distinguish known afflictions. These include discriminating features, consistent features and variable features of known afflictions. The features are in classification domains. As shown, the records are in phenomenological, anatomic, pathologic, pathophysiologic and etiological test domains.

As an example, consistent features are those that occur 75% of the time and variable features are those that occur less than 75% of the time. These need not be consistent with the discriminator domain, i.e. cerebral spinal fluid glucose is consistently low in bacterial tuberculous meningitis. Each record (table) reflects what is believed to be the best way of distinguishing between these and similar entities, again reflecting the state-of-the-art. Contributor experts identify discriminant, consistent, and variable features. Exemplary database records are given below.

Stenonic Valvular Heart Disease

Dr. Thomas Albrecht prepared the following record (table) describing the features of the present invention for Valvular Stenonic Heart Disease.

| Discriminating Features | Consistent Features | Variable Features |
|---|---|---|
| | Pulmonary Stenosis | |
| 1. Echocardiographic Appearance | 1. Systolic Murmur | 1. EKG Changes
2. Ejection Clicks |
| | Aortic Stenosis | |
| 1. Echocardiographic Appearance | 1. Systolic Murmur | 1. EKG Changes
2. Chest Pains
3. Ejection Clicks |
| | Mitral Stenosis | |
| 1. Echocardiographic Appearance | 1. Diastolic Murmur | 1. Opening Sound
2. Pulmonary Edema
3. Wheezing (cardiac) |
| | Tricuspid Stenosis | |
| 1. Echocardiographic Appearance | 1. Diastolic Murmur | 1. Hepatomegalty
2. Clicks |

Errors of Metabolism

Dr. William Nyhan used the classification features of the present invention for distinguishing in-born errors of metabolism from one another using patho-physiologic discriminators.

| Discriminating Feature | Consistent Features | Variable Features |
|---|---|---|
| | LESCH-NYHAN SYNDROME | |
| Complete deficiency of hypoxanthine-guanine phosphoribosyltransferase | 1. Hyperuricemia
2. Urisosuria
3. Mental retardation
4. Spastic cerebral palsy
5. Chroeoasthetosis
6. Self-mutilation | 1. Convulsions
2. Hemraturia
3. Urinary tract stones
4. Urinary tract infections
5. Tophi
6. Urate nephropathy
7. Vomiting |
| | PURINE NUCLEOSIDE PHOSPHORYLASE DEFICIENCY | |
| 1. Deficiency of PNP | 1. Immunodeficiencies
2. T-cell depletion
3. Infections
4. Hypouricemia
5. Nucleoside accumulation | Neurologic abnormalities |
| | PHENYLKETONURIA | |
| 1. Deficient hepatic phenylalanine
2. Elevated plasma phenylalanine
3. Depressed plasma tyrosine | 1. Mental retardation
2. Diminished pigment
3. Phenylpyruvic aciduria
4. Phenyllactic aciduria
5. Phenylacetyglutamic aciduria | 1. Vomiting
2. Eczematoid rash
3. Odd odor
4. Restriction fragment length polymorphism |
| | ABNORMALITIES IN THE METABOLISM OF BIOPTERIN | |
| 1. Defective activity of dihydropteridine reductase
2. Evidence of deficient synthesis of tetrahydro-biopterin | 1. Hyperphenylalaninemia
2. Degenerative neurologic disease
3. Convulsions
4. Spasticity | 1. Rigidity
2. Tremors
3. Dystonic movements |
| | MAPLE SYRUP URINE DISEASE | |
| Complete deficiency of branched-chain ketoacid | 1. Elevated concentrations of leucine, isoleucine and valine | 1. Maple syrup odor to urine
2. Mental retardation |

-continued

| Discriminating Feature | Consistent Features | Variable Features |
|---|---|---|
| decarboxylase | 2. Positive dintrophenyl-thydrazine test of urine<br>3. Branched-chain ketoaciduria | 3. Spasticity<br>4. Opisthotonos<br>5. Coma<br>6. Convulsions<br>7. Hypodense cerebral myelin |
| DISORDERS OF PROPIONATE METABOLISM | | |
| PROPIONICACIDEMIA | | |
| Deficiency of propionyl-CoA carboxylase | 1. Methylcitraturia<br>2. Hydroxypropionaturia<br>3. Propionicacidemia<br>4. Recurrent episodes of ketosis and acidosis, leading to coma and potentially fatal illness<br>5. Osteoporosis<br>6. Vomiting<br>7. Hypotonia<br>8. Anorexia<br>9. Monilasis | 1. Hyperammonemia<br>2. Anemia<br>3. Hyperglycinemia, hyperglycinuria<br>4. Pathologic fractures<br>5. Mental retardation<br>6. Immunodeficiency<br>7. Abnormal MRI of the basal ganglia |
| METHYLMALONICACIDEMIA | | |
| Deficiency of methylmalonyl CoA mutase | As in propionicacidemia, plus failure to thrive | As in propionic academia |
| MULTIPLE CARBOXYLASE DEFICIENCY | | |
| 1. Deficiency of holocarbosylase synthetase<br>2. Deficiency of biotinidase | As in propionicacidemia plus<br>1. Alopecia<br>2. Dermatosis<br>3. Lacticacidemia, lacticaciduria<br>4. Deficient leukocyte carboxylases<br>5. Convulsions in biotinidase deficiency<br>6. Sensorineural deafness and visual defects in biotinidase deficiency<br>7. Ataxia in biotinidase deficiency | As in propionicacidemia |
| ISOVALERICACIDEMIA | | |
| 1. Isovaleryglycinuria<br>2. Deficiency of isovaleryl-CoA dehydrogenase | 1. Episodes of acute illness<br>2. Ketoacidosis<br>3. Neutropenia, thrombocytopenia | 1. Acrid "sweaty foot" odor<br>2. Mental Retardation<br>3. Hyperammonemia<br>4. Anemia<br>5. Ataxia<br>6. Convulsions |
| GLUTARICACIDURIA | | |
| Glutaricaciduria | 1. Spasticity<br>2. Convulsions<br>3. Cerebral degeneration<br>4. Involuntary movements | Metabolic acidosis |
| colspan="3" 3-HYDROXY-3-METHYLGUTARICACIDURIA | | |
| 1. 3-Hydroxy-3-methylglutaricaciduria<br>2. 3-Hydroxy-3-methylglutaryl-CoA lyase deficiency | 1. 3-Methylglutaconicaciduria<br>2. 3-Methylglutaricaciduria<br>3. Hypoketotic hypoglycemia<br>4. Acute overwhelming illness<br>5. Metabolic acidosis<br>5. Lethargy or coma | 1. Lacticaciduria<br>2. Lacticacidemia<br>3. Hyperammonemia<br>4. Hypotonia<br>5. Hepatomegaly<br>6. Vomiting<br>7. Elevated liver functions tests<br>8. Convulsions<br>9. Cerebral atrophy |
| Y-HYDROXYBUTRICACIDURIA | | |
| Succinic semialdehyde dehydrogenase deficiency | 1. Y-Hydroxybutyricacidura<br>2. Convulsions<br>3. Ataxia<br>4. Mental Retardation | 1. Hyperactivity<br>2. Somnolence |
| NONKETOTIC HYPERGLYCINEMIA | | |
| 1. Elevated CSF and plasma glycine ration | 1. Hyperglycinemia<br>2. Hyperglycinuria<br>3. Neonatal coma and apnea | 1. Hypertonia<br>2. Hypotonia<br>3. Increased deep tendon |

-continued

| Discriminating Feature | Consistent Features | Variable Features |
|---|---|---|
| | 4. Myoclonic seizures (infantile spasms) 5. EEG burst suppression pattern 6. Cerebral atrophy | reflexes 4. Hiccuping |

HOMOCYSTINURIA

| Discriminating Feature | Consistent Features | Variable Features |
|---|---|---|
| 1. Homocystinuria 2. Cysathionine synthase deficiency | Mixed disulfide of cysteine and homocysteine in urine | 1. Hypermethioninemia 2. Ectopia lentis 3. Mental retardation 4. Thromboembolic phenomena 5. Failure to thrive 6. Genu valgum 7. Osteoporosis |

UREA CYCLE DISORDERS

| Discriminating Feature | Consistent Features | Variable Features |
|---|---|---|
| 1. OTC deficiency 2. CPS deficiency 3. Arginnosuccinic synthase deficiency 4. Argininosuccinase deficiency | 1. Oroticaiduria in OTC deficiency 2. Hyperammonenmia in OTC deficiency 3. Hyperglutaminemia in OTC deficiency 4. Coma in OTC deficiency CPS deficiency as in OTC, except for orotic aciduria Citrullinemia as in OTC deficiency, plus 5. Citrullinemia 6. Citrullinemia as in OTC deficiency, plus 7. Increased concentrations of argininosuccinate in urine and CSF | 1. Hyperalaninemia 2. Hyperaspartic acidemia 3. Convulsions 4. Mental retardation 5. Trichorrhexis nodosa (in argininocuccinic aciduria) |

ARGININEMIA

| Discriminating Feature | Consistent Features | Variable Features |
|---|---|---|
| 1. Arginase deficiency 2. Argininemia | 1. Spastic diplegia 2. Developmental delay 3. Hypertonia 4. Opisthotonus 5. Involuntary movements | 1. Hyperammonemia 2. Hepatomegaly 3. Abnormal liver function tests 4. Convulsions 5. EEG abnormalities |

Current knowledge permitted the use of only one discriminator When the defective gene is identified for each of these disorders, then each can be discriminated from the other based on genotype. This will enhance etiologic discrimination from the other based on genotype. This will enhance etiologic discrimination and will more powerfully distinguish similar entities from one another.

Classification Record of the Epilepsies

Dr. Joseph Sirven and Dr. Michael Sperling used the same system to classify the epilepsies, but the result is a much different record. In this case, discriminators are phenomenologically based, again reflecting the state-of-the-art. A phenomenologically based system is probably the most appropriate to use at this state-of-the-art rather than to use one that is etiologically derived. The universal use of this system will probably unfortunately impede its evolution into a system which is etiologically based, although usage alone should not preclude developing an etiologically based system. Practicality also plays an important operative function in domain selection.

Classification Records of Brain Injuries

Feature Table: Acute Severe Traumatic Brain Injury
　Discriminating Features
　　Loss of consciousness in all severe traumatic brain injuries, except purely focal injuries.
　　Deepening coma flowing a rostral-caudal progression from hemispheric dysfunction through diencephalic, midbrain, pontine, and medullary stages.
　　Trauma sufficient to produce the injury.
　Consistent Features
　　Contusion of the undersurfaces of the temporal and frontal lobes, and of the anterior poles of the temporal lobes, whatever the site of impact.
　　Brainstem dysfunction associated invariably with hemispheric dysfunction.
　　Deepening coma associated with the progressive appearance of flexor posturing, extensor posturing, and finally flaccidity.
　　Some degree of anoxic-ischemic brain injury.
　Variable Features
　　Contusion of the brain on the side opposite the point of impact. (Contre-coup lesions).
　　In an individual child, the depth of coma is only roughly correlated with the severity of injury. Focal traumatic injury and anoxia account for some of this variability.

Feature Table: Mild Traumatic Brain Injury
　Discriminating Features
　　Confusion and amnesia are the hallmarks of MTBI.
　　Trauma sufficient to explain the complaints.
　Consistent Features
　　Loss of consciousness less than 30 minutes.

Post traumatic amnesia less than 24 hours.

Nausea, vomiting, dizziness, headache, blurred vision, sleep disturbance, quickness of fatigue, lethargy.

Impairments in memory, thinking, attention and concentration, behavioral and mood lability.

CT and other imaging studies may show contusion or epidural, subdural or subarachnoid bleeding.

Variable Features

Mild or minor head injury, or concussion, is sometimes associated with acute deterioration or lasting sequelae.

Some children over report and others under report symptoms.

Most symptoms of MTBI resolve entirely within 2 or 3 months.

Symptoms of MTBI often are endorsed by uninjured children.

Sideline examination of children with sports related injuries may help identify those at greater risk when returning to play.

A small number of children with loss of consciousness and amnesia should be transported to a center prepared to diagnose and treat sever traumatic brain injury.

Feature Table: Deterioration Following Acute Brain Injury

Discriminating Features

Subacute decreasing level of consciousness is the most sensitive indicator of progressive brain and brainstem compromise.

Increased brain volume is due to greater quantities of extracellular fluid (vasogenic edema), intracellular fluid (cytotoxic edema), or blood (hyperemia).

Collections of free blood in the epidural space, in the subdural space, in the ventricles, or within the brain parenchyma.

Consistent Features

Increased intracranial pressure.

CT picture of small ventricles and lucent brain with blurring of the gray-white borders.

Focal neurological signs.

Hemiparesis with a supratentorial hematoma.

Pupillary and eye movement abnormalities and motor signs suggest a posterior fossa hematoma.

Seizures.

Gradually developing third nerve palsy suggests an intracerebral hematoma and may herald impending uncal herniation.

Variable Features

Obliteration of the perimesencephalic cisterns may be seen in incipient or actual herniation.

Seizures worsen brain swelling, but are more likely to occur if there is some focal injury to the brain.

Electrolyte abnormalities may be due to diabetes insipidus or to the syndrome of inappropriate antidiuretic hormone secretion.

A hypermetabolic state with arterial hypertension and tachycardia.

Epidural hematomata often are associated with fractures of the skull and rupture of an artery lying near the skull.

Subdural hematomata often are associated with marked underlying brain injury owing to the shearing forces involved in the formation of the hematoma.

Intracerebral bleeding often complicates focal contusion and lacerations and may be delayed by hours or days following the injury.

Retinal and preretinal hemorrhages may accompany intracerebral hematomata, especially those involving acceleration/decelerations injuries and Retinal and preretinal hemorrhages suggest non accidental trauma.

Feature Table: Recovery from Traumatic Brain Injury

Discriminating Features

The hallmarks of traumatic brain injury include impairments in memory, organization, speed of thinking, attention and concentration, affective control and irritability, motivation, judgment and socialization.

To establish that a specific event caused the signs and symptoms of traumatic encephalopathy, it is necessary to document that the signs and symptoms appeared following the specific injury.

Memory of the events of the accident and immediately after is lost in all but the mildest injuries.

Consistent Features

Motor deficits including spasticity, disorders of tone and posture, movement disorders, ataxia, and deficits in the planning and execution of complex coordinated movements.

Attention and concentration problems, impulsivity, distractibility, and motor hyperactivity.

Difficulties with reasoning, and tracking complex concepts, and multi-tasking.

Slow and inefficient cognitive processing.

Short-term memory problems, memory retrieval difficulties and shrinking retrograde amnesia.

Language problems including comprehension, visual perceptual, naming, and expressive difficulties. Nonaphasic speech disturbances also may occur. More complex problems with understanding and relating stories and humorous material are often present.

Behavior and emotional changes, which may include explosive behavior, catastrophic anxiety, or intractable indifference.

Variable Features

Focal neurological deficits.

Visual field limitations

Problems with discriminatory touch and stereognosis.

Hearing loss.

School performance below that expected from standardized testing given in a one-on-one setting.

Online Computer System

FIG. 1 depicts a computer 10 which accesses a data base 11 of records each having the discriminating, consistent and variable features of the present invention as depicted. The features are in classification domains which include phenomenological 11a, anatomic 11b, pathologic 11c, pathophysiologic 11d and etiological 11e domains.

Figure 2:
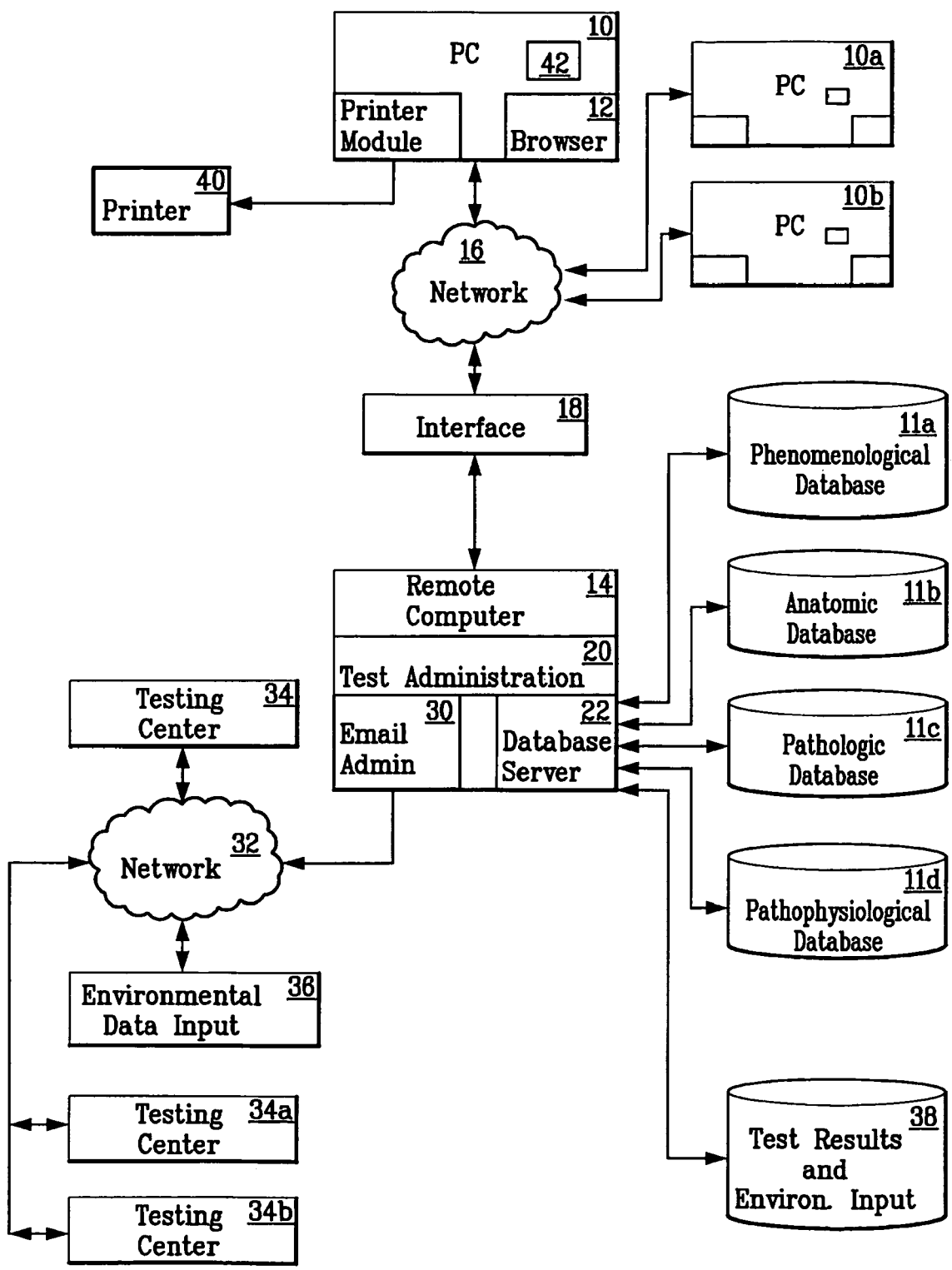
FIG. 2 depicts a computer system for the online diagnosis of a patient in accordance with the present invention.

While the invention has great utility in the stand alone computer system shown in FIG. 1, the preferred embodiment is in an online computer system shown in FIG. 2. The system of FIG. 2 has the advantage of being capable of continual and accurate updates of a central database. The computer system shown in FIG. 2 is more fully described in U.S. application Ser. No. 10/909,032 filed Jul. 30, 2004, which is a continuation-in-part of Ser. No. 10/849,755 filed May 20, 2004. The foregoing application is incorporated herein by reference in its entirety.

For ease of reference portions of the foregoing application which apply specifically to the present invention are repeated herein.

A personal computer (PC) 10 at which a doctor can access the databases includes a browser 12. Personal computer 10 accesses a remote computer 14 through a network 16. Netscape Navigator or Microsoft Internet Explorer are common browsers. Network 16 is the internet, a local area network, or a virtual private network (VPN). A plurality of PC's including 10a and 10b access computer 14 through network 16.

Remote computer 14 runs a network interface program 18 such as Microsoft Interface Server or an Apache Server. Interface program 18 accepts instructions from the network 16. The instructions pass through to a test administration program 20 which is running on the remote computer 14. The interface program 18 uses the HTTPS protocol to transfer instructions from personal computer 10 to the remote computer 14.

Test administration program 20 includes a database server 22 which accesses the records in the phenomenological domain database 11a, the anatomic domain database 11b, the pathologic domain database 11c, the pathophysiologic database 11d and so on.

E-mail administration module 30 sends data related to a doctor's order through a network 32 to a testing center 34 and environmental data input 36.

A testing center 34, comprises a laboratory and a computer system. The testing center 34 performs the tests in an anonymous manner and returns the results of the tests over a network 32 to the database 38.

Similarly, patient screening for environmental data is digitized at the data input 36. These inputs are all transmitted over network 32 to the remote computer 14 and thence to the database 38.

In the laboratory a blood sample is drawn and tested for the usual tests including a series of tests commonly referred to as Chem 20. The results of these tests are digitized. In addition to these tests, DNA in the blood sample is analyzed and put in a format which can be correlated with known genetic disorders.

EXAMPLES

1. Sinusitis

Physicians are taught to reason from the general to the specific. For example, a patient has fever. What are the likely causes? For a variety of reasons, sinusitis is suspected. The physician goes online, checks the diagnostic nosology and is given the discriminating, consistent and variable features for sinusitis created by an expert or by expert consensus. These features are determined from a cat-scan of the sinuses. These are used to confirm or reject the physician's initial suspicion.

2. Valvular Heart Disease

In the case of valvular heart disease, the presenting symptom, unlike a fever, is a heart murmur. The doctor goes online to check the criteria for each kind of valvular heart disease that produces a murmur. The doctor pulls up the discriminating, consistent and variable features of valvular heart disease. In an iterative series of tests and deductions, the doctor can make a reliable, speedy and accurate diagnosis. The diagnostic nosology of the present invention is, in essence, a diagnostic computer database.

Like the example of sinusitis, the patient with valvular heart disease would come to the physician because someone had listened to their chest and heard a heart murmur. Then suspecting that there was a leak across a valve, the most definitive test would be an echocardiogram. The domain test of echocardiography is used to discriminate the various types of valvular heart disease one from another by the echocardiographic appearance. A cardiogram gives a visual image of the valve and the leakage across the valve. Unlike sinusitis which is commonly presented to a physician with a fever, a heart problem is something that would be uncovered in a routine physical exam and so it represents a different type of general presenting problem. Just like sinusitis the physician is attempting to distinguish or discriminate between different kinds of valvular heart disease. He refers to an expert opinion on line and determine how one distinguishes one type of valvular heart problem from another using the echocardiogram. It is a more sophisticated discriminator than simply a cat-scan of the sinuses. The echocardiographic appearance is the discriminating feature for each one of pulmonary stenosis, aortic stenosis, mitral stenosis and tricuspid stenosis. See the record (table) for stenonic valvular heart disease given above.

The patient would undergo an echocardiogram because a professional listened to his chest and heard a murmur. An echocardiogram which is similar to a cat-scan or x-ray except it uses an echo imaging system as opposed to a x-ray imaging system. The cardiographic appearance that is characteristic of aortic stenosis, that is characteristic of mitral stenosis and characteristic of tricuspid stenosis is shown. Each one of these echocardiographic appearances has some distinct features. The echocardiographic appearance for aortic stenosis, mitral stenosis, and tricuspid stenosis is different, but the consistent feature for mitral stenosis is a diastolic murmur. The variable features would be different for each one of these. The patient with mitral stenosis would also have an opening sound, a pulmonary edema and a wheezing. The doctor can diagnose that the patient has mitral stenosis. Three things are required for this diagnosis. 1) The patient has the typical cardiographic appearance; 2) The individual has a diastolic murmur as opposed to a systolic murmur; 3) In addition there is an opening sound; the patient has symptoms of pulmonary edema and wheezing. That's all consistent with mitral stenosis and not consistent with pulmonary stenosis, aortic stenosis or tricuspid stenosis.

3. Lesch-Nyhan Syndrome

The domain is pathophysiology. There is a complete absence of a specific enzyme which is a transferase. A specific enzyme is deficient and there are elevations of uric acid. Uric acid crystals are in the patient's urine. The individual is mentally retarded, they have spastic cerebral palsy, they have unusual movements, they are self-mutilators consistently. That implies more than 75% of the time. Variable features include convulsions, hematuria, urinary tract stones and so on. This distinguishes this particular syndrome from other similar syndromes. This represents multi-dimensional thinking. When you think about a fever and what are the different causes of fever, that really is almost uni-dimensional, but here the physician has to first make a decision as to how he is going to discriminate it from similar conditions and what he is going to use as his discriminating domain. Is it going to be an x-ray, a bio-chemical test? The patient may actually come in to the physician because they are mentally retarded but there are many different causes of mental retardation, only one of which is Lesch-Nyhan Syndrome.

There are other abnormalities of metabolism, but the biochemical domain distinguishes purine nucleoside deficiencies, phenylketonuria, abnormalities in biopterin and maple syrup urine disease. Biochemical tests discriminate one from another.

The present invention allows the doctor to discriminate between these five entities, Lesch-Nyhan and the other four. The discriminating domain is the biochemical domain unlike valvular heart disease where the discriminating domain is the echocardiographic appearance and sinusitis where the appearance on a C-T scan is the discriminating domain.

In summary, for each database record, experts will: (1) agree on features which discriminate one group of similar diseases/disorders from one another (e.g. enzyme deficiency). A determination is made as to what classification domain this falls in, e.g. genetic disorder—defective gene, pathophysiologic domain? A determination is made as to whether a single discriminator will suffice or are multiple discriminators required reflective of the state-of-the-art (e.g. genetic disorder, single discriminator is sufficiently robust)? If multiple discriminators are needed (i.e. a criterion-based system), are inclusionary as well exclusionary criteria to be used? What consistent and variable features should be used? What should be the relative frequency to distinguish between consistent and variable features?

While particular embodiments have been shown and described, it will be appreciated that other modifications are possible. For example, the diagnostic nosology of the present invention can be used in an automated diagnosis system with low human intervention. The diagnostic nosology of the present invention can be used for remote diagnosis when the patient is not accessible to a doctor. Also, by use of the diagnostic nosology of the present invention, greater reliance can be placed on paramedic professionals to maximize the efficient use of doctors' time. The following claims, therefore, are intended to cover all such modifications within the true spirit and scope of the invention.

What is claimed is:

1. A method of diagnosing a patient comprising:
testing said patient to determine features of his affliction;
accessing a computer database of records of discriminating features of known afflictions, said records being arranged nosologically in classification domains;
inputting to a computer the features of said patient's affliction as determined by said testing; and
analyzing at least one of said classification domains in said database and said features of said patient's affliction to determine the singular affliction that is distinguished from other afflictions by said features of said patient's affliction.

* * * * *